United States Patent
Shah et al.

(10) Patent No.: US 10,420,730 B2
(45) Date of Patent: *Sep. 24, 2019

(54) L-MENTHOL DOSAGE FORMS HAVING A PROTEINACEOUS COATING FOR ENHANCED STORAGE STABILITY

(71) Applicant: Zx Pharma, LLC, Boca Raton, FL (US)

(72) Inventors: Syed M. Shah, Boca Raton, FL (US); Fred Hassan, Boca Raton, FL (US)

(73) Assignee: Zx Pharma, LLC, Boca Raton, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/876,465

(22) Filed: Oct. 6, 2015

(65) Prior Publication Data
US 2016/0022597 A1    Jan. 28, 2016

Related U.S. Application Data

(63) Continuation of application No. 14/524,326, filed on Oct. 27, 2014, now Pat. No. 9,192,583, which is a
(Continued)

(51) Int. Cl.
*A61K 36/534*    (2006.01)
*A61K 36/23*    (2006.01)
(Continued)

(52) U.S. Cl.
CPC .......... *A61K 9/5057* (2013.01); *A61K 9/0053* (2013.01); *A61K 9/2054* (2013.01);
(Continued)

(58) Field of Classification Search
None
See application file for complete search history.

(56) References Cited

U.S. PATENT DOCUMENTS 2,366,749 A    1/1945    Ofner et al.
3,515,781 A *  6/1970    Steinberg ............. A61K 9/0043
                                                          424/455
(Continued)

FOREIGN PATENT DOCUMENTS

CN    101596166 B    8/2011
CN    1886119 B    4/2015
(Continued)

OTHER PUBLICATIONS

Eccles, "Menthol: effects on nasal sensation of airflow and the drive to breathe", Rhinitis, Common Cold and Nasal Research Centre, Cardiff School of Biosciences, pp. 210-214 (2003).*
(Continued)

*Primary Examiner* — Ernst V Arnold
*Assistant Examiner* — Kyung S Chang
(74) *Attorney, Agent, or Firm* — Christopher M. Ramsey; GrayRobinson, P.A.

(57) ABSTRACT

A storage stable L-menthol composition including a tablet, caplet, capsule, or sachet dosage form has therein a core containing crystalline L-menthol and at least one pharmaceutical excipient. A proteinaceous coating of a continuous film of proteinaceous material is over the core. The film is effective to substantially prevent the crystalline L-menthol from volatilizing and leaving the core when stored at a temperature of 40 degrees C. and 75% relative humidity from between 1 day to 30 days. The dosage form contains an effective amount of the crystalline L-menthol for treating a gastrointestinal disorder.

33 Claims, 2 Drawing Sheets

Related U.S. Application Data continuation of application No. 14/033,713, filed on Sep. 23, 2013, now Pat. No. 8,895,086.

(60) Provisional application No. 61/880,294, filed on Sep. 20, 2013, provisional application No. 61/815,073, filed on Apr. 23, 2013.

(51) Int. Cl.

| | | |
|---|---|---|
| A61K 36/82 | (2006.01) | |
| A61K 9/50 | (2006.01) | |
| A61K 9/00 | (2006.01) | |
| A61K 9/48 | (2006.01) | |
| A61K 31/045 | (2006.01) | |
| A61K 9/20 | (2006.01) | |

(52) U.S. Cl.
 CPC .......... *A61K 9/2081* (2013.01); *A61K 9/2095* (2013.01); *A61K 9/4808* (2013.01); *A61K 9/4833* (2013.01); *A61K 9/4866* (2013.01); *A61K 9/5026* (2013.01); *A61K 9/5073* (2013.01); *A61K 9/5089* (2013.01); *A61K 31/045* (2013.01); *A61K 36/23* (2013.01); *A61K 36/534* (2013.01); *A61K 36/82* (2013.01)

(56) References Cited

U.S. PATENT DOCUMENTS

| | | |
|---|---|---|
| 4,687,667 A | 8/1987 | Rhodes et al. |
| 4,786,505 A | 11/1988 | Lovgren et al. |
| 5,362,745 A | 11/1994 | Graziella |
| 5,397,573 A | 3/1995 | Kajs et al. |
| 5,418,010 A | 5/1995 | Janda et al. |
| 5,498,423 A | 3/1996 | Zisapel |
| 5,688,510 A | 11/1997 | Nakamichi et al. |
| 5,840,332 A | 11/1998 | Lerner et al. |
| 6,139,877 A | 10/2000 | Debregeas et al. |
| 6,306,435 B1 | 10/2001 | Chen et al. |
| 6,365,185 B1 | 4/2002 | Ritschel et al. |
| 6,423,349 B1 | 7/2002 | Sherratt et al. |
| 6,531,152 B1 | 3/2003 | Lerner et al. |
| 6,632,451 B2 | 10/2003 | Penhasi et al. |
| 6,726,927 B2 | 4/2004 | Chen |
| 6,972,132 B1 | 12/2005 | Kudo et al. |
| 7,041,316 B2 | 5/2006 | Chen |
| 7,048,945 B2 | 5/2006 | Percel et al. |
| 7,115,282 B2 | 10/2006 | Shefer et al. |
| 7,670,619 B2 | 3/2010 | Mihaylov |
| 7,670,624 B2 | 3/2010 | Tsutsumi et al. |
| 7,790,215 B2 | 9/2010 | Sackler et al. |
| 7,790,755 B2 | 9/2010 | Akiyama et al. |
| 7,803,817 B2 | 9/2010 | Kostadinov et al. |
| 7,829,122 B2 | 11/2010 | Bruna et al. |
| 7,838,027 B2 | 11/2010 | Rao et al. |
| 8,337,811 B1 | 12/2012 | Sung et al. |
| 8,361,439 B1 | 1/2013 | Sung et al. |
| 8,524,257 B2 | 9/2013 | Nowak et al. |
| 8,535,640 B1 | 9/2013 | Sung et al. |
| 8,545,880 B2 | 10/2013 | Li et al. |
| 8,568,776 B2 | 10/2013 | Shah et al. |
| 8,574,544 B1 | 11/2013 | Sung et al. |
| 8,808,736 B2 | 8/2014 | Shah et al. |
| 9,393,279 B2 | 7/2016 | Shah et al. |
| 2001/0038863 A1 | 11/2001 | Jaenicke et al. |
| 2002/0114832 A1 | 8/2002 | Herrmann et al. |
| 2002/0192285 A1 | 12/2002 | Mulye |
| 2002/0192885 A1 | 12/2002 | Miyasaka |
| 2003/0040539 A1 | 2/2003 | Zisapel |
| 2003/0143272 A1 | 7/2003 | Waterman |
| 2003/0207851 A1 | 11/2003 | Wei |
| 2004/0052846 A1 | 3/2004 | Prater et al. |
| 2004/0062778 A1 | 4/2004 | Shefer et al. |
| 2004/0191402 A1 | 9/2004 | Stawski et al. |
| 2005/0069579 A1 | 3/2005 | Kamaguchi et al. |
| 2005/0129761 A1 | 6/2005 | Venkata Ramana Rao et al. |
| 2005/0164987 A1 | 7/2005 | Barberich |
| 2005/0169987 A1* | 8/2005 | Korber .................. C07C 29/76 424/464 |
| 2005/0181047 A1 | 8/2005 | Romero |
| 2005/0202079 A1 | 9/2005 | Bielski et al. |
| 2005/0281876 A1 | 12/2005 | Li et al. |
| 2006/0009465 A1 | 1/2006 | Edgar et al. |
| 2006/0210631 A1 | 9/2006 | Patel et al. |
| 2006/0217489 A1 | 9/2006 | Yako et al. |
| 2006/0246134 A1 | 11/2006 | Venkatesh |
| 2006/0257469 A1 | 11/2006 | Bulka |
| 2006/0280795 A1 | 12/2006 | Penhasi et al. |
| 2007/0048366 A1 | 3/2007 | Chen et al. |
| 2007/0231388 A1 | 10/2007 | Anstett-Klein et al. |
| 2007/0292510 A1 | 12/2007 | Huang |
| 2008/0139510 A1 | 6/2008 | Rose |
| 2008/0152719 A1 | 6/2008 | Petereit et al. |
| 2008/0166416 A1 | 7/2008 | Lizio et al. |
| 2008/0199518 A1 | 8/2008 | Ku et al. |
| 2008/0299199 A1 | 12/2008 | Bar-Shalom et al. |
| 2009/0004262 A1 | 1/2009 | Shaw et al. |
| 2009/0004281 A1 | 1/2009 | Nghiem et al. |
| 2009/0137670 A1 | 5/2009 | Kramer et al. |
| 2009/0227670 A1 | 9/2009 | Berg |
| 2009/0238905 A1 | 9/2009 | Gurney et al. |
| 2009/0246301 A1 | 10/2009 | Ehrenpreis et al. |
| 2010/0119601 A1 | 5/2010 | McCarty |
| 2010/0183713 A1 | 7/2010 | Tsutsumi et al. |
| 2010/0203134 A1 | 8/2010 | Chenevier et al. |
| 2010/0297251 A1 | 11/2010 | Timmons et al. |
| 2010/0298379 A1 | 11/2010 | Jacobsen |
| 2011/0053866 A1 | 3/2011 | Duffield et al. |
| 2011/0064830 A1 | 3/2011 | Piotrowski |
| 2011/0081451 A1 | 4/2011 | Siegel et al. |
| 2012/0128764 A1 | 5/2012 | Venkatesh et al. |
| 2012/0207842 A1 | 8/2012 | Shah et al. |
| 2012/0277323 A1 | 11/2012 | Kumar et al. |
| 2012/0301541 A1 | 11/2012 | Haronsky et al. |
| 2012/0301546 A1 | 11/2012 | Hassan |
| 2013/0230597 A1 | 9/2013 | Cook et al. |
| 2014/0178468 A1 | 6/2014 | Shear et al. |

FOREIGN PATENT DOCUMENTS

| | | | |
|---|---|---|---|
| DE | 202012000910 U1 | 1/2013 | |
| EP | 0015334 B1 | 5/1982 | |
| EP | 0556346 B1 | 7/2001 | |
| EP | 1953625 A | 8/2008 | |
| EP | 1958625 A1 | 8/2008 | |
| JP | 53039503 | 10/1978 | |
| JP | 62226926 | 10/1987 | |
| JP | 2000247870 | 9/2000 | |
| JP | 2007197378 | 8/2007 | |
| JP | 2008127349 | 6/2008 | |
| JP | 2010189443 | 9/2010 | |
| JP | 5201819 | 6/2013 | |
| JP | 2015024986 | 2/2015 | |
| KR | 20060118452 A | 11/2006 | |
| WO | 9513794 | 5/1995 | |
| WO | 9959544 | 11/1999 | |
| WO | 2005027878 A1 | 3/2005 | |
| WO | 2005032513 A2 | 4/2005 | |
| WO | WO2006/097427 A1 * | 9/2006 | ............... A61K 8/25 |
| WO | 2007012856 A1 | 2/2007 | |
| WO | 2008057802 A2 | 5/2008 | |
| WO | 2008134807 A1 | 11/2008 | |
| WO | 2009077749 A1 | 6/2009 | |
| WO | 2010144943 A1 | 12/2010 | |
| WO | 2011111027 A2 | 9/2011 | |
| WO | 2012109216 A1 | 8/2012 | |
| WO | 2012170488 A1 | 12/2012 | |

(56) References Cited

FOREIGN PATENT DOCUMENTS

| WO | 2012170611 A1 | 12/2012 |
| WO | 2014065390 A1 | 5/2014 |

OTHER PUBLICATIONS

Tran et al., New findings on melatonin absorption and alterations by pharmaceutical excipients using the Ussing chamber technique with mounted rat gastrointestinal segments, International Journal of Pharmaceuticals 378 (2009) pp. 9-16, Bioavailability Control Laboratory, College Pharmacy, Kangwon National University, Chuncheon 200-701, Republic of Korea.

Trimble et al., Heightened Visceral Sensation in Functional Gastrointestinal Disease is not site-specific, Digestive Diseases and Sciences, vol. 40, No. 8, Aug. 1995, pp. 1607-1613.

White et al., A pharmacokinetic comparison of two delayed-release peppermint oil preparations, Colpermin and Mintec, for treatment of the irritable bowel syndrome, International Journal of Pharmaceutics, vol. 40, 1987, pp. 151-155, Ipswich, United Kingdom.

Yuasa et al., Whisker Growth of L-menthol in coexistence with various excipents, International Journal of Pharmacutics 203, (2000), pp. 203-210, Tokyo, Japan.

Abdul et al., A Flexible Technology of Modified-Rlease Drugs: Multiple-Unite Pellet System (MUPS), J Controlled Release 147: 2-16 (2010).

Alexander Ford, Nicholas J. Talley, Brennan M Spiegel, Amy E Foxx-Orenstein, Lawrence Schiller, Eamonn M Quigley, Paul Moayyedi; Effect of Fibre, Antispasmodics, and Peppermint Oil in the Treatment of Irritable Bowel Syndrome: Systematic Review and Meta-Analysis; BMJ Research; Sep. 24, 2008.

Baranuskiene et al., Flavor Retention of Peppermint (*Mentha piperita* I.) Essential Oil Spray-Dried ni Modified Starches during Encapsulation and Storage, J. Agric. Food Chem., 2007, 55, 3027-3036.

Benes et al., Transmucosal, Oral Controlled-Release and Transdermal Drug Administration in Human Subjects: A Corssover Study with Melatonin, Journal of Pharmaceutical Sciences / 1115, vol. 86, No. 10, Oct. 1997.

Bogentoft et al., Influence of Food on the Absorption of Acetylsalicylic Acid From Enteric-Coated Dosage Forms, European J.Clin. Pharmacol., 14, 351-355, 1978.

Cellulose acetate phthalate enter coating (enerexusa.com/articles/enteric_coating.htm., last visit Feb. 6, 2014).

Chourasia et al., Pharmaceutical Approaches to Colon Targeted Drug Delivery Systems, J Pharm Pharmaceut Sci 6: 33-66 (2003).

Clark et al., Variations in Composition of Peppermint Oil in Relation to Production Areas, Economic Botany 35(1), 1981, pp. 59-69, Bronx, NY, USA.

Committee for Proprietary Medicinal Products, Note for Guidance On Quality of Modified Release Products: A: Oral Dosage Forms, B: Transdermal Dosage Forms, Jul. 29, 1999, The European Agency for the Evaluation of Medicinal Products, London.

Dey et al., Multiparticulate Drug Deliver Systems for Controlled Release, Tropical Journal of Pharmaceutical Research, Sep. 2008; 7(3): 1067-1075, Pharmacotherapy Group, Faculty of Pharmacy, University of Benin, Benin City, 300001 Nigeria.

Digenis, Geroge A., The in vivo behavior of multiparticulate versus single unit dose formulations, presented at Capsugel's Symposium in Seoul (Apr. 10, 1990) and Tokyo (Apr. 12, 1990).

Dong et al., Effect of processing parameters on the formation of spherical multinuclear microcapsules encapsulating peppermint oil by coacervation, Journal of Microencapsulation, Nov. 2007; 24(7): 634-646.

Faroongsarng et al., The Swelling & Water Uptake of Tablets III: Moisture Sorption Behavior of Tablet Disintegrants, Drug Development and Industrial Pharmacy, 20(5), 779-798, (1994).

Final Report on the Safety Assessment of *Mentha piperita* (Peppermint) Oil, *Mentha piperita* (Peppermint) Leaf Extract, *Mentha piperita* (Peppermint) Leaf, and *Mentha piperita* (Peppermint) Leaf Water, International Journal of Toxicology, 2001 20:61, online version at http;//ijt.sagepub.com/content/20/3/_suppl/61.

Galeotti et al., Menthol: a natural analgesic compound, Neuroscience Letters 322 (2002), pp. 145-148, Florence, Italy.

Grigoleit et al., Gastrointestinal clinical pharmacology of peppermint oil, Phytomedicine 12, (2005), pp. 607-611, Wiesbaden, Germany.

International Search Report dated Jan. 29, 2014 for PCT/US2013/000217.

International Search Report dated Feb. 4, 2014 for PCT/US2013/061146.

International Search Report dated Feb. 6, 2014 for PCT/US2013/061141.

International Search Report of PCT/US2012/024110.

International Search Report of PCT/US2012/041224.

International Search Report of PCT/US2012/22848.

International Search Report of PCT/US12/41226.

Juergens, et al., The Anti-Inflammatory Activity of L-Menthol Compared to Mint Oil in Human Monocytes In Vitro: A Novel Perspective for Its Therapeutic Use in Inflammatory Diseases, Eur J. Med Res (1998) 3: 539-545, Dec. 16, 1998.

Kellow et al., Altered Small Bowel Motility in Irritable Bowel Syndrome is Corrected with Symptoms, Gastroenterology, 1987, vol. 92, pp. 1885-1893, Rochester, Minnesota, USA.

Kim et al. (The Influence of Surelease and Sodium Alginate on the In-Vitro Release of Tamsulosin Hydrochloride in Pellet Dosage Form., J Pharm Pharmacol, Jun. 2005; 57(6): 735-42.

Kline et al., Enteric-Coated pH-dependent peppermint oil capsules for the treatment of irritable bowel syndrome in children, J Pediatr 2001; 138: 125-8.

Lee et al, Design and evaluationof an oral controlled release delivery systme for melatonin in humans subjects, International Journal of Pharmaceutics 124 (1995) 119-127, College of Pharmacy, Kangwon National University, Chuncheon, South Korea, Department of Pharmaceutics, College of pHarmacy, Oregeon State University, Corvallis, OR 97331-3507, USA, Department of Psychiatry, School of Medicine, Oregon Health Sciences University, Portland, OR, USA.

Lee et al., Formulation and Release Characteristics of Hydroxpropyl Methycellulose Matrix Tablet Containing Melatonin, Drug Development and Industrial Pharmacy, 25(4), 493-501 (1999), Biological Rhythm and Controlled Release Laboratory, College of Pharmacy, Kangwon National University, Chuncheon 200-709, Korea.

Liu et al., pH-resonsive amphiphilic hydrogel networks with IPN structure; A strategy for controlled drug release, International Journal of Pharmaceutics 308 (2006) 205-209, Department of Applied Chemistry, School of Science, Northwestern Polytechnic University, Xi'an 710072, PR China.

MacPherson et al., More than cool: promiscuous relationships of menthol and other sensory compounds, Mol. Cell. Neurosci, vol. 32, 2006, pp. 335-343.

McIntyre et al., Melatonin Rhythm in Human Plasma and Saliva, Journal of Pineal Research 4:177-183 (1987), Psychoendocrine Research Unit, Department of Psychiatry, Austin Hospital Heidelbert (I.M.M., T.R.N., G.D.B.), and Department of Psychology, Brain Behaviour Research Institute, Latrobe University, Bundoora (S.M. A.), Victoria, Australia.

Menthols (inchem.org/documents/sids/sids/MENTHOLS.pdf, lat visit Feb. 6, 2014).

Micklefield, et al., Effects of Peppermint Oil and Caraway Oil on Gastroduodenal Motility, Phytother. Res. 14, 20-23 (2000).

Office Action for U.S. Appl. No. 14/033,713 dated May 14, 2014.

Office Action for U.S. Appl. No. 14/033,737 dated Apr. 23, 2014.

Office Action for U.S. Appl. No. 14/064,685 dated Sep. 24, 2014.

Office Action for U.S. Appl. No. 14/064,685 dated Mar. 7, 2014.

Office Action for U.S. Appl. No. 14/524,326, dated Apr. 23, 2015.

Pilbrant et al., Development of an oral formulation of omeprazole, Scand J. Gastroenterol, 1985, vol. 20 (suppl. 108, pp. 113-120, Molndal, Sweden.

Pilbrant, Formulation of proton pump inhibitors, Capsugel Library, BAS 153-d.

(56) References Cited

OTHER PUBLICATIONS

Pittler et al., Peppermint Oil for Irritable Syndrome: A Critical Review and Metaanalysis, The American Journal of Gastroenterology, vol. 93, No. 7, 1998, 1131-1135.

Rees et al., Treating Irritable Bowel Syndrome with Peppermint Oil, British Medical Journal, Oct. 6, 1979.

Rohloff et al., Effect of Harvest Time and Drying Method of Biomass Production, Essential Oil Yield, and Quality of Peppermint (*Mentha x piperita* L.), J. Agric. Food Chem., 2005, vol. 53, pp. 4143-4148 Hedmark, Norway.

RXMED: Pharmaceutical Information—Colpermin, Peppermint Oil Symptomatic Relief of Irritable Bowel Syndrome, Jan. 4, 2010.

Sibanda et al., Experimental Design for the Formulation and Optimization of Novel Cross-Linked Oilispheres Developed for In Vitro Site-Specific Release of Mentha piperita Oil, AAPS PharmSciTech 2004; 5(1) Article 18 (http://www.aapsharmscitech.org, submitted Nov. 5, 2003, Accepted Feb. 18, 2004.

Somerville et al., Delayed release peppermint oil capsules (Colpermin) for the spastic colon syndrome: a pharmacokinetic study, Br. J. clin. Pharmac., (1984), vol. 18, pp. 638-640, Ipswich, United Kingdom.

Stevens et al., The short term natural history of irritable bowel syndrome: a time series analysis, Behav. Res. Ther., vol. 35, No. 4, pp. 319-326, 1997, Albany, NY, USA.

The Migrating Motor Complex, http://www.vivo.colostate.edu/hbooks/pathphys/digestion/stomach/mmcomplex.html. (last visit Jan. 4, 2016).

Thompson, Shaun, List of Proton Pump Inhibitors, Mar. 12, 2011, http://www.livestrong.com/article/26705-list-proton-pump-inhibitors.

Bigi, A., Cojazzi, S. Panzavolta, K., Rubini, N., Roveri, N. ., "Mechanical and Thermal Properties of Gelatin Films at Different Degrees of Glutaraldehyde Crosslinking":Biometerials 22; 2001; pp. 764-768.

Eccles, "Menthol: Effects On Nasal Sensation Of Airflow And The Drive To Breath", Rhinitis, Common Cold and Nasal Research Centre, Cardiff School of Biosciences; pp. 210-214; 2003.

Hawthorne, M; The Actions of Peppermint Oil and Menthol on Calcium Channel Dependent Processes in Intestinal, Neuronal and Cardiac Preparations; Department of Biochemical Pharmacology, State University of New York; Oct. 14, 1987.

Office Action for U.S. Appl. No. 14/524,648 dated Mar. 24, 2016.

Office Action for U.S. Appl. No. 14/918,042 dated Jan. 8, 2016.

Singh, Saranjit; Rao, KV. Rama; Venugopal, Rao, K.; Manikandan, R.; "Alteration in Dissolution Characteristics of Gelatin-Containing Formulations"; Pharmaceutical Technology, Apr. 2002.

Office Action for U.S. Appl. No. 14/918,042 dated May 11, 2016.

Yu Songhua et al.; "Investigation on Preparation and Stability of Gelatin Coated Garlic Oil Pellets"; The Chinese and Foreign Health Abstract, No. 25, vol. 7, pp. 88-89; Nov. 23, 2010.

\* cited by examiner

L-MENTHOL DOSAGE FORMS HAVING A PROTEINACEOUS COATING FOR ENHANCED STORAGE STABILITY

CROSS-REFERENCE TO RELATED APPLICATIONS

This is a continuation of application Ser. No. 14/524,326, filed Oct. 27, 2014, which is continuation of application Ser. No. 14/033,713, now U.S. Pat. No. 8,895,086, filed Sep. 23, 2013, which claims priority to U.S. provisional application 61/815,073, filed Apr. 23, 2013 and U.S. provisional application 61/880,294, filed Sep. 20, 2013. These priority applications are incorporated by reference herein in their entireties.

FIELD

This relates to therapeutic L-menthol compositions, and, more particularly, to L-menthol compositions with enhanced storage stability.

BACKGROUND

Terpenes are a large class of organic compounds that are often naturally produced by plants and provide the fragrant aroma of plant-derived essential oils. Many terpenes and their associated essential oils are widely known to be pharmaceutically active. Because of this, people have developed various ways of administering terpenes to treat many different ailments.

By way of example, peppermint oil is widely used to address gastrointestinal problems such as irritable bowel syndrome because it inhibits the smooth muscles in the gastrointestinal tract from contracting. Unfortunately, however, if peppermint oil is released in the stomach, it is absorbed quickly and can upset the stomach. To overcome this problem, others have developed oral delayed-release peppermint oil formulations that allow the peppermint oil to pass into the intestines before it is released.

A common method for delivering peppermint oil to the intestines is to load a hollow capsule with peppermint oil and coat the capsule with an enteric coating. The enteric coating prevents the capsule from dissolving in the stomach and releasing the peppermint oil too early.

These single-unit enteric coated capsules have several drawbacks, including extremely variable gastric emptying time (from 60 to 570 minutes), dose dumping, and their inability to exit from the contracted pylorus due to the presence of food in the stomach. These problems can be addressed by developing multiparticulate compositions containing terpene-based active ingredients. In U.S. patent publication 2012/0207842 and corresponding WIPO publication WO 2012/109216, we described a multiparticulate formulation containing high-purity L-menthol. Some of the particulates in those formulations included a core containing L-menthol, a subcoating over the core, and an enteric coating over the subcoated core. The preferred subcoating was hydroxyl propyl methyl cellulose or "HPMC." The multiparticulate formulations described in that application provided the release profile that we desired and worked well for some applications, but are not optimized for all applications. U.S. patent publication 2012/0207842 and WIPO publication WO 2012/109216 are both incorporated by reference in their entireties.

We found that it is difficult to make multiparticulate formulations containing terpene-based active ingredients because terpenes are very volatile. If the multiparticulate core containing terpene-based active ingredients is heated or stored for extended periods, much above room temperature, the terpenes will permeate, evaporate or sublimate and leave the core. This made processing the cores very difficult, especially when it came time to cure the enteric coating on the cores at elevated temperatures. For our L-menthol formulations, we resorted to low temperature processing techniques.

SUMMARY

Through extensive research, we discovered that using a proteinaceous coating prevents the L-menthol based active ingredients in the core from permeating, evaporating, or sublimating at elevated temperatures and for long periods of time. Accordingly, we have invented new compositions containing terpene-based active ingredients that have enhanced storage stability.

A storage stable L-menthol composition includes a tablet, caplet, capsule, or sachet dosage form having therein a core containing crystalline L-menthol and at least one pharmaceutical excipient. A proteinaceous coating of a continuous film of proteinaceous material is over the core. The film is effective to substantially prevent the crystalline L-menthol from volatilizing and leaving the core when stored at a temperature of 40 degrees C. and 75% relative humidity from between 1 day to 30 days. The dosage form contains an effective amount of the crystalline L-menthol for treating a gastrointestinal disorder.

A method of making a storage stable L-menthol composition includes forming a solid core by combining crystalline L-menthol and at least one pharmaceutical excipient. A continuous film of a liquid proteinaceous material is applied over the core. The liquid proteinaceous material is dried over the core to form a proteinaceous coating effective to substantially prevent the crystalline L-menthol from volatilizing and leaving the core when stored at a temperature of 40 degrees C. and 75% relative humidity from between 1 day to 30 days.

A method of treating a gastrointestinal disorder includes administering to a patient in need thereof an effective amount of a storage stable L-menthol composition comprising a tablet, caplet, capsule, or sachet dosage form having therein a core containing crystalline L-menthol and at least one pharmaceutical excipient. A proteinaceous coating of a continuous film of proteinaceous material is over the core. The film being effective to substantially prevent the crystalline L-menthol from volatilizing and leaving the core when stored at a temperature of 40 degrees C. and 75% relative humidity from between 1 day to 30 days.

These and other aspects, embodiments, and advantages will be better understood by reviewing the accompanying figures and the Detailed Description of Embodiments.

DETAILED DESCRIPTION OF EMBODIMENTS

Figure 1:
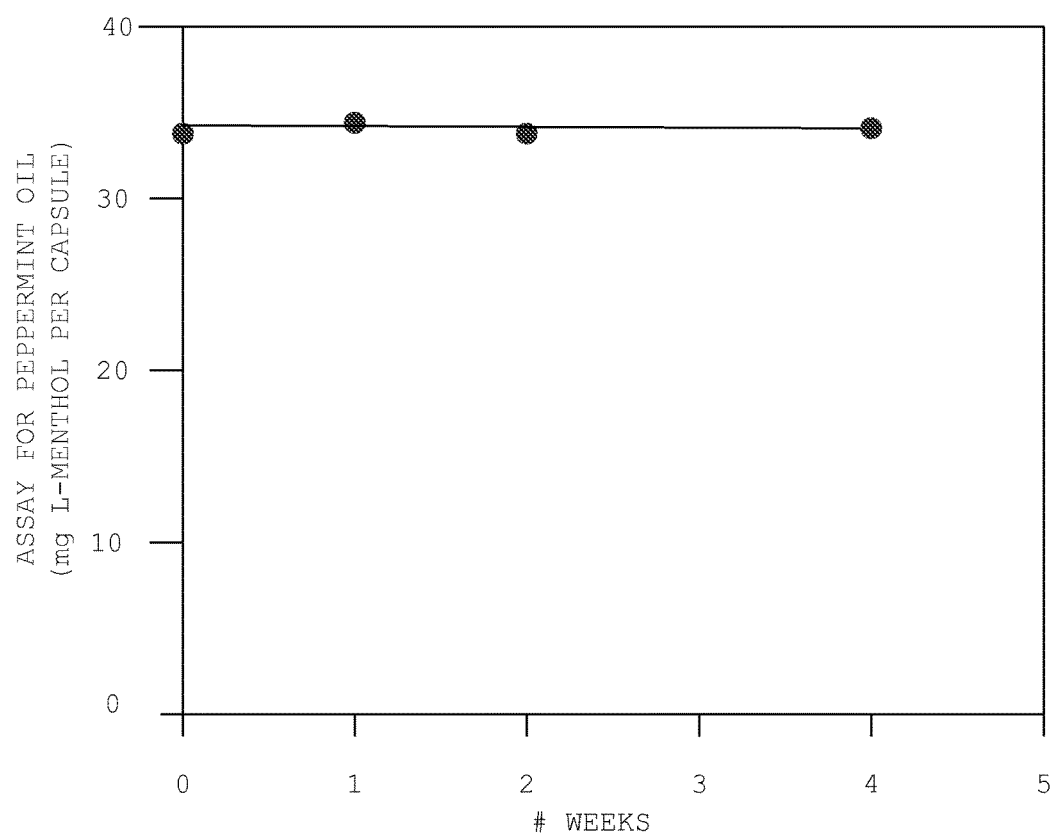
FIG. 1 is a graph showing the results of an accelerated stability assay for a multiparticulate composition according to an embodiment stored at 40 degrees C. and 75% relative humidity for four weeks.

In the Summary and Detailed Description of Embodiments reference is made to particular features including method steps. It is to be understood that the disclosure of the in this specification includes all possible combinations of such particular features, even if those combinations are not explicitly disclosed together. For example, where a particular feature is disclosed in the context of a particular aspect or embodiment, that feature can also be used, to the extent possible, in combination with and/or in the context of other particular aspects and embodiments The term "comprises" is used herein to mean that other ingredients, steps, etc. are optionally present. When reference is made herein to a method comprising two or more defined steps, the steps can be carried in any order or simultaneously (except where the context excludes that possibility), and the method can include one or more steps which are carried out before any of the defined steps, between two of the defined steps, or after all of the defined steps (except where the context excludes that possibility).

In this section, embodiments will be described more fully. The embodiments may, however, take in many different forms and should not be construed as limited to the embodiments set forth herein.

A multiparticulate composition aspect is first described. The multiparticulate composition is adapted to carry biologically active ingredients to the intestines (duodenum, small intestine, or colon) and includes a plurality of particulates that are preferably spheroidal in shape and are sized to fit through the pyloric sphincter when it is in a relaxed state. The diameter of each particulate is preferably in the range of about 0.1 mm to about 3 mm or, about 1 mm to about 2.5 mm, or less than about 1.4 mm.

The particulates are preferably formed from a spheroidal core that is coated with several coating layers, including a subcoating and an enteric coating. The subcoating encompasses the core and physically separates the core from the enteric coating. The enteric coating is positioned about the subcoating in such a way that the subcoating is located between the core and enteric coating. The particulates may also include one or more additional coatings such as a sealant coating, finish coating, or a color coating on the enteric coating.

The core contains the primary active ingredient(s), which are terpene-based substances such as terpenes, terpenoids, and/or one or more essential oils. The core may also contain secondary active ingredients such as one or more different terpenes, terpenoids, and/or essential oils. Terpene-based substances that may be used as secondary active ingredients include but are not limited to caraway oil, orange oil, ginger oil, turmeric oil, curcumin oil, and fennel oil, among others.

One of the preferred terpene-based active ingredients is L-menthol from an L-menthol source that is at least about 80% pure L-menthol, such as liquid, solid, or crystalline L-menthol. L-menthol is typically a crystalline material at room temperature, has a melting point at standard pressure of about 42°-45° C., and may undergo sublimation at slightly above room temperature. The 80% pure L-menthol may be dissolved in an essential oil such as caraway oil to form a liquid mixture, prior to mixing with acceptable excipients and water to make a wet mass while the cores are being formed.

The term "solid L-menthol" means L-menthol in its solid form, preferably in its crystalline form. In the crystalline form, L-menthol is substantially free of undesirable impurities. Although it may not always be necessary, it is preferred that the starting material for L-menthol appear as visually perceptible L-menthol crystals that are then ground into a polycrystalline powder. Micronizing the L-menthol is often advantageous because doing so produces more L-menthol surface area, which improves L-menthol's aqueous solubility. It is preferred, however, that the L-menthol be micronized without raising the temperature of the L-menthol enough to degrade the L-menthol molecules, cause L-menthol to melt, or cause L-menthol to sublimate. A suitable technique for producing micronized L-menthol crystals involves jet milling.

Essential oils such as peppermint oil, caraway oil, orange oil, fennel oil etc. are liquid at room temperature. They are usually formulated as liquids in a capsule, with an enteric-coating over the capsule. We discovered that essential oils can be mixed with a cellulosic filler and a binder to make a dough or wet mass, but the dough formed by simply mixing these materials together does not produce a core with the desired strength for subcoating and further processing. By adding water to the wet mass, we produced cores containing terpene-based active ingredient(s) that were robust enough for subsequent processing.

The core may also contain one or more antioxidants that can maintain the purity of the terpene-based active ingredients. This is useful when the terpene-based active ingredients that are employed can oxidize to form undesirable derivatives. Examples of antioxidants that may be used include, but are not limited to tocopherol (vitamin E,) BHT (butylated hydroxy toluene), BHA (butylayted hydroxy anisole), and ascorbic acid.

The core may also contain other non-terpene active ingredients such as plant based polyphenolic compounds, including, for example, green tea extract, aloe vera.

The core may also include other active ingredients that behave synergistically with certain terpenes, such as L-menthol, to treat gastrointestinal disorders. These other active ingredients include drugs typically used to treat various gastrointestinal issues including proton pump inhibitors, anti-inflammatories, and immune suppressors. Combining L-menthol with these other active ingredients improves their efficacy because L-menthol enhances their permeation into the intestinal walls.

Examples of PPIs include, but are not limited to omeprazole, lansoprazole, dexlansoprazole, esomeprazole, pantoprazole, rabeprazole, and ilaprazole. Including a PPI is preferred when the L-menthol in the core is dissolved in caraway oil.

Examples of anti-inflammatory drugs include aminosalicylates, including 5-aminosalicylate (5-ASA). Examples of 5-ASA are sulfasalazine, mesalamine, olsalazine and balsalazide. These work by decreasing the inflammation at the level of the lining of the gastrointestinal tract. However they do not address the pain and other symptoms associated with ulcerative colitis or Crohn's disease. The 5-ASAs are poorly absorbed. They are more effective when they are released and locally delivered to the ileum (for Crohn's disease) or colon (for ulcerative colitis). The L-menthol in combination with aminosalicylates (in the core) and with an enteric coat specific for delivery at the appropriate pH between pH 6.8 and 7.5 is useful for treating gastrointestinal disorders. We expect this combination to address the needs of the patients with the above disorders. Enteric coatings suited to these PPI-containing formulations include hypromellose acetate succinate coatings such as AQOAT AS-HF, AQOAT AS-HG and poly(meth)acrylate-based coatings such as EUDRAGIT FS 30D or EUDRAGIT S-10.

Examples of immune suppressors include corticosteroids such as prednisone and methylprednisolone. Corticosteroids non-specifically suppress the immune response. These drugs have significant short- and long-term side effects. They need to be delivered to the ileum (for Crohn's disease) or colon (for ulcerative colitis) for maximum efficacy. A combination of L-menthol with prednisone, prednisolone or methylprednisolone, formulated in the core, with an enteric coat specific for delivery at the appropriate pH between pH 6.8 and 7.5 is useful for treating gastrointestinal disorders, such as ulcerative colitis or crohn's disease. This activity may allow the patient to receive a lower dose of the corticosteroid in combination with L-menthol as compared to the corticosteroid by itself. The unique activities of L-menthol help relieve abdominal pain, cramps, and diarrhea. Enteric coatings suitable for these immune suppressor-containing formulations include AQOAT AS-HF, AQOAT AS-HG, EUDRAGIT FS 30D or EUDRAGIT S-100.

The core may also include pharmaceutically acceptable fillers, stabilizers, binders, surfactants, processing aids, and/or disintegrants. By way of example only, suitable materials for performing these functions are provided.

Preferred fillers include cellulosic filler materials such as microcrystalline cellulose, dibasic calcium phosphate, and/or another pharmaceutically acceptable filler.

Preferred binders include cellulosic water soluble polymers such as methyl cellulose, starch, hydroxypropyl cellulose, gelatin, polyvinylpyrrolidone, polyethylene glycol, and/or another pharmaceutically acceptable binder.

Because some terpene-based active ingredients, such as L-menthol, are not very water soluble, it may be advantageous to include a surfactant as a solubilizing agent. Preferred solubulizing agents include but are not limited to polysorbate and/or sodium lauryl sulfate. Advantageously when polysorbate 80 is used, it may also enhance absorption of terpene-based active ingredients into the plasma.

Suitable processing aids include pharmaceutically acceptable processing aids for improving the flowability of the core materials during processing. Preferred processing aids include, but are not limited to, colloidal silicon dioxide, talc, magnesium stearate, stearin, and/or another pharmaceutically acceptable processing aid.

Preferred disintegrants include, but are not limited to, croscarmellose sodium, polyvinylpyrrolidone (crospovidone) sodium starch glycolate, and/or another pharmaceutically acceptable processing aid. A preferred amount of disintegrant is about 0.05% w/w to about 20% w/w of the enteric coated cores.

In a particularly preferred embodiment of the multiparticulate composition, the core comprises about 10% w/w to about 35% w/w of one or more terpene-based active ingredients; about 25% w/w to about 75% w/w filler; and about 1.5% w/w to about 10% w/w binder. Here the % w/w is the weight of the active ingredient or excipient relative to the total weight of the enteric coated multiparticulates.

Once the core is formed, the subcoating is applied along its exterior surface to form a substantially continuous thin film that forms a barrier between the core and the enteric coating that is applied after the subcoating. One of the particularly advantageous features is the use of a proteinaceous material as a subcoating material. Examples of proteinaceous materials that may be used include proteins such as, but not limited to casein, whey protein, soy protein, and various types of gelatin (Type A, Type B or derivatives of gelatin) or proteinaceous materials that have protein-like structures. In a preferred embodiment, the material used to form the subcoating is a solution containing at least about 50% of the proteinaceous material dispersed in a solvent. The solvent is preferably, but not necessarily water. A particularly preferred proteinaceous material is Type A gelatin.

The proteinaceous subcoating is preferably applied to the core in liquid form and subsequently dried on the core. When dry, the subcoating adheres to the core. Examples of the liquid form of the proteinaceous subcoating material include melts and gels. When dry, the subcoating forms a continuous film over the core and provides a barrier between the core and enteric coating.

One of the problems we discovered while developing multiparticulate compositions containing terpene-based active ingredients is that the terpenes sometimes penetrated the conventional subcoating materials and came in contact with the enteric coating if the temperature was elevated (25 degrees C.-50 degrees C.) or the composition was stored for a long period of time. This somewhat reduced the effectiveness of the enteric coating and amount of active ingredient in the core. By using the proteinaceous subcoating, we have substantially eliminated this problem.

The multiparticulate composition is preferably adapted to have a controlled release profile once it enters the intestines. To treat certain gastrointestinal disorders, it is highly desirable to avoid releasing greater than 20% of the total active ingredients in the composition over a 2 hour period in a solution with a pH below 4, which simulates the liquid environment in the stomach. If the composition releases greater than 20% of the active ingredients present, it can cause adverse effects because of the pharmacological action of the terpenes in the stomach. For peppermint oil and L-menthol, for example, this can cause dyspepsia, erosive esophagitis, acid reflux or GERD (gastro-esophageal reflux disease).

Because it is often desirable to be able to ship products in non-refrigerated vehicles and store them for a long period of time, we set out to develop a multiparticulate composition that is stable when stored at 40 degrees C. and 75% relative humidity, from between 1 day to 30 days, and even longer. Using the proteinaceous subcoating allowed us to achieve this objective.

Gelatin typically melts at about 35 degrees C., which is below the normal human body temperature of about 37 degrees C. Given this, one might expect that, if a multiparticulate composition, including a gelatin subcoating, is heated above 35 degrees C., the subcoating will melt and release the active ingredients from the core. We observed, however, that gelatin subcoated multiparticulate compositions did not release the terpene-based active ingredients from the core even when heated above 35 degrees C. This is a particularly unexpected result that provides numerous advantages.

Because the proteinaceous subcoating prevents volatile terpene components from being released from the core even when heating above the melting point of the proteinaceous material, by applying the proteinaceous subcoating, one does not have to avoid heating the subcoated cores during processing. One scenario in which this is advantageous is when the enteric coating is applied. Enteric coating polymers have a glass transition temperature ($T_g$) that is often above 35 degrees C. After being applied to a core, enteric coated particulates are preferably heated above $T_g$ so that the enteric coating polymer can cure, thereby achieving optimum enteric protection of the core. Thus, using the proteinaceous subcoating between the core and enteric coating allows one to achieve optimum enteric protection without releasing the terpene-based active ingredients from the core.

In certain preferred embodiments of the multiparticulate composition, the subcoating is applied to the core as a gelatin-containing subcoating solution. The solvent may be any solvent in which gelatin is soluble, such as water. In a preferred embodiment, the subcoating solution comprises about 5% to about 30% w/w gelatin and about 70% to about 95% solvent. When the subcoating solution is allowed to dry around the core, the solvent evaporates, leaving a thin gelatin film that adheres to the core and forms a barrier between the core and enteric coating.

Surprisingly, in our experiments, drying the core containing the essential oil and water, at about 15 degrees C. to about 25 degrees C. did not result in significant loss of the terpene-based active ingredients as the water was being removed by fluid bed drying.

The enteric coating is applied over the subcoating. In a preferred embodiment, the enteric coating is about 2% w/w to about 35% w/w of the enteric coated particulate. A preferred enteric coating material is a methacrylic acid based material such as a methacrylic acid based co-polymer. Examples of suitable methacrylic acid based copolymers include EUDRAGIT L30D-55 (Evonik Rohm GmbH, Germany) or KOLLICOAT MAE 30 DP (BASF SE, Germany). KOLLICOAT MAE 30 DP is a methacrylic acid-ethyl acrylate co-polymer. These materials may be combined with other materials such as plasticizers for forming an enteric coating solution. In a typical embodiment, the enteric coating solution comprises about 5% w/w to about 35% w/w water, and the enteric-coated dried multiparticulates contain 0.5% w/w to about 5% w/w plasticizer, about 0.05% w/w to about 5% w/w anti-adherent, and about 2% w/w to about 35% w/w methacrylic acid copolymer. By way of example only, a suitable plasticizer is triethyl citrate and a suitable anti-adherent is PLASACRYL T20 (Emerson Resources, Inc., Norristown, Pa.). PLASACRYL T20 is an emulsion of anti-tacking agent and plasticizer and contains water, glyceryl monostearate, triethyl citrate and polysorbate 80.

In a particular preferred embodiment of the multiparticulate composition, the particulates in the multiparticulate composition comprise: (a) a core comprising about 15 w/w to about 35% w/w active ingredient(s), about 40% w/w to about 75% w/w microcrystalline cellulose, and about 2% w/w to about 10% w/w methyl cellulose; (b) a gelatin film subcoating over the core; and (c) an enteric coating over the subcoated core. The gelatin film subcoating is preferably about 3.5% w/w to about 35% w/w of the enteric coated particulates. The enteric coating is preferably about 3.5% w/w to about 35% w/w of the enteric coated particulates.

The enteric-coated particulates may be coated with a finish coat. The finish coat is used, for example, to overcome the mucoadhesive properties of some enteric coating materials, which make the multiparticulates stick together during processing, storage, or dispensing through a tube for enteral feeding. The finish coat is preferably a cellulosic derivative such as HPMC (hydroxyl propyl methyl cellulose), HPC (hydroxyl propyl cellulose), CMC (carboxy methyl cellulose), or another pharmaceutically acceptable finish coating material. When used, the finish coat is preferably about 1% to 10% w/w of the finished multiparticulate.

The active ingredient release profile in the body can be varied to treat different disorders. By way of example, L-menthol and peppermint oil can be used to treat a plethora of gastrointestinal disorders such as irritable bowel syndrome, inflammatory bowel disease, and functional dyspepsia, but it is best to release the active ingredients at a certain point in the gastrointestinal treat each disorder.

To treat gastrointestinal disorders associated with irritable bowel syndrome, the multiparticulate composition is formulated to minimize the amount of active ingredients, such as L-menthol or peppermint oil, released into the stomach and colon, so that most of the active ingredient is released in the small intestine. Preferably, 20% or less of the active ingredients are released into the stomach and 20% or less of the active ingredients are released into the colon. Also, the active ingredients are preferably gradually released over the course of about 4 to about 8 hours after the multiparticulates pass the pyloric sphincter into the small intestine in order to deliver the active ingredients locally in the small intestine. This release profile treats gastrointestinal disorders by stabilizing the digestive system and alleviating the symptoms associated with disorders such as irritable bowel syndrome.

To treat a gastrointestinal disorder such as functional dyspepsia (classified as a gastro-duodenal disorder), the multiparticulate composition is formulated so that the terpene-based active ingredients are rapidly released, after the multiparticulates pass through the stomach and the pylorus, over the course of about 0 to about 2 hours, in order to deliver the active ingredients locally to the duodenum section of the small intestine to help stabilize the digestive system and/or alleviate the symptoms associated with functional dyspepsia. Preferably, 20% or less of the active ingredient(s) is released in the stomach and 20% or less of the active ingredient(s) is released in the jejunum and ileum sections of the small intestine (which follow the duodenum) and the colon.

To treat a gastrointestinal disorder such as inflammatory bowel disease, including ulcerative colitis or Crohn's disease), the multiparticulate composition is formulated so that the terpene-based active ingredients are rapidly released, after the multiparticulates pass through the stomach and the small intestine, over the course of about 4 to about 6 hours, in order to deliver the active ingredients locally to the colon to attenuate the inflammatory response and/or alleviate the symptoms associated with inflammatory bowel disease. Preferably, 30% or less of the active ingredient(s) is released in the stomach and small intestine greater than 70% of the active ingredient(s) is released in the first 2 hours after the multiparticulates reach the pH of the colon.

A multiparticulate composition particularly geared to treat functional dyspepsia includes a combination of L-menthol or peppermint oil and caraway oil. In this embodiment, the core is formulated to contain a disintegrant to facilitate the rapid release of the active ingredients in the duodenum. Preferred disintegrants include, but are not limited to croscarmellose sodium, polyvinylpyrrolidone (crospovidone) and/or sodium starch glycolate. The amount of disintegrant is preferably about 1% w/w to 20% w/w of the finished multiparticulate. In order to ensure even distribution of the active ingredient(s), the L-menthol and/or peppermint oil is dissolved in the caraway oil prior to mixing with excipients, prior to formation of the cores.

An effective amount is an amount that is sufficient to affect a disease or process in the body. A daily dose of a multiparticulate composition containing L-menthol is preferably about 10 mg to about 400 mg of L-menthol, split into 2 or three doses per day. Each dosage form may contain between 5 mgs and 140 mgs of L-menthol, more preferably, about 80-100 mgs of 1-menthol per capsule.

It should be understood that where this disclosure makes reference to treating a gastrointestinal disorder, that the terms "treat," "treating, or any other variation of the word "treat" include prevention or management of the gastrointestinal disorder.

A daily dose of a multiparticulate composition containing peppermint oil is about 20 mg to about 1200 mgs of peppermint oil, split into 2 or three doses per day. Each dosage form may contain between 10 mgs and 140 mgs of peppermint oil, more preferably, about 90-110 mg of peppermint oil.

A daily dose of a multiparticulate composition containing L-menthol and caraway oil contains about 15 mg to about 700 mgs of peppermint oil plus 15 mg to 500 mgs of caraway oil, split into 2 or three doses per day. Each dosage form may contain between 10 mgs and 70 mgs of L-menthol plus 5 mg to 50 mg of caraway oil, more preferably, about 40-50 mg of L-menthol plus 20-30 mg of caraway oil.

Doses of the multiparticulate composition may be administered sporadically when needed for treating acute inflammations of the gastrointestinal tract or may be administered as part of a long term regimen for treating GI disorders such as irritable bowel syndrome, functional dyspepsia, gastroparesis or inflammatory bowel disease. A treatment subject may be a human or animal.

The enteric coated multiparticulates are prepared into a suitable pharmaceutical or medical food dosage form such as a capsule, tablet or sachet, or are mixed with an acidic food vehicle and directly fed through a feeding tube. A typical dosage form contains about 400 mg of the particulates, but, depending on the desired dosage, this amount may be adjusted. Acidic food vehicles include citrus juices and foods such as, for example, apple sauce and apple juice.

The multiparticulate composition is preferably formulated to be administered enterally, such as orally or through a feeding tube, to a human or animal subject to ensure that the subject receives an effective amount of terpene-based active ingredients over the course of several hours after ingestion.

A preferred method of making the multiparticulate composition is now described. The core is typically prepared by wet granulating the core materials into a wet mass, extruding the wet mass to form an extrudate, cutting the extrudate into a plurality of core pieces, and spheronizing the core pieces. The spheronized core pieces are then dried in a dryer such as a fluid bed dryer to remove most of the water. If desired the dried spheronized cores are then sieved to separate cores of different sizes.

The dried spheronized cores are then coated with the proteinaceous subcoating material. One way to apply the subcoating material to the cores is to prepare a subcoating solution and spray the subcoating solution onto the cores. There are various conventional methods for doing this, but the preferred method is Wurster coating or fluid bed coating (top spray or bottom spray). The subcoating solution is subsequently allowed to dry over the cores, leaving each core coated with a thin, continuous proteinaceous film. If desired, the subcoated cores are sieved to separate them into different sizes.

The enteric coating is then applied to the subcoated cores. One means of applying the enteric coating is to spray it onto the subcoated cores. There are various conventional methods for doing this, but the preferred method is Wurster coating or fluid bed coating. The enteric coated particulates are subsequently dried. During the enteric coating process, the cores are preferably heated in an environment that is about 20 degrees C. to about 50 degrees C. to cure the enteric coating materials above their $T_g$.

A finish coating may be applied over the enteric coated particulates if desired. One way to apply the finish coating is to spray it onto the enteric coated cores. There are various conventional methods for doing this, but the preferred method is Wurster coating or fluid bed coating.

Another method aspect of is a method of treating a gastrointestinal disorder. This method comprises administering a multiparticulate composition including a proteinaceous subcoating between the core and enteric coating to a subject. As mentioned above, there are various means of administration that can be used, including enteral administration, administration via a feeding tube, and administration in food.

The multiparticulate composition can be enterally administered through use of a conventional oral dosage form such as a tablet, caplet, capsule, or sachet, among others.

Another enteral means for administering the multiparticulate composition, either orally or via a tube, is as a medical food product. In the medical food product, the multiparticulate composition is blended with an acidic food vehicle such as apple juice or another acidic vehicle that prevents premature release of the active ingredients.

Although many of the more specific embodiments we have described include peppermint oil, L-menthol, and/or caraway oil, one having ordinary skill in the art will understand that the use of a proteinaceous subcoating is generally applicable to many other pharmaceutically active terpene-based active ingredients because they present the same difficulty; namely, because they are volatile, it is difficult to prepare them in heat stable multiparticulate dosage forms.

EXAMPLES

This section provides specific examples of the multiparticulate composition and method aspects. These examples are provided to illuminate certain preferred aspects and embodiments, but the scope is not limited to what these examples teach.

Example 1: Preparation of a Multiparticulate Composition

The core was prepared using microcrystalline cellulose (MCC) commercially available under the name AVICEL PH 102 (FMC Corp., Philadelphia, Pa.), methylcellulose commercially available under the name METHOCEL A15LV (Dow Chemical Co., Midland, Mich.), distilled peppermint oil, and USP purified water.

33.25 kg MCC, 1.75 kg methyl cellulose, and 15 kg peppermint oil were blended with water to form a wet mass. The wet mass was granulated in a high shear granulator. The granulated wet mass was then extruded and spheronized. The spheronized particles were subsequently dried in a fluid bed dryer to form uncoated cores. The drying temperature was about 16 degrees C.

The uncoated cores were Wurster coated with 37 kg of a subcoating composition containing about 15% acid bone gelatin and 85% USP water and dried.

The subcoated cores were Wurster coated with 31 kg of a 20% w/w enteric coating suspension containing KOLLICOAT MAE 30 DP, PLASACRYL T20, triethyl citrate USP, and purified water USP. The dry solids weight of amount KOLLICOAT MAE 30 DP was approximately 5.4 kg. The dry solids weight of triethyl citrate was approximately 0.28 kg. The dry solids weight of PLASACRYL T20 was approximately 0.5 kg. The enteric coated cores were then dried at about 40 degrees C.

The enteric coated cores were Wurster coated with 26 kg of a finish coat solution containing about 10% w/w hydroxyl propyl methyl cellulose and 90% water USP and dried at about 40 degrees C.

Example 2: Stability Testing of the Multiparticulate Composition of Example 1

The multiparticulate composition described in Example 1 was subsequently tested to ensure that the gelatin subcoating prevented the peppermint oil from evaporating and leaving the core when stored at elevated temperatures over a long period of time.

In the first set of experiments, we prepared capsules containing the multiparticulate composition and stored them at degrees C. and 75% relative humidity for four weeks. Each week, we measured the amount of peppermint oil in a selection of the capsules. FIG. 1 shows the results of this study as a graph of the number of milligrams of L-menthol per capsule as a function of time. The results show that the amount of L-menthol in the capsules remained more or less constant at about 34 mg during the four week period. This proves that the gelatin subcoating maintains the integrity of the core.

In the second set of experiments, we simulated the gastrointestinal environment and measured the dissolution profile of the multiparticulate composition to ensure that the enteric coating worked and that almost all of the peppermint oil would be released from the core within about 8.5 hours. This was a conventional two stage dissolution study in which the sample was placed in an acidic medium (0.1 N HCl) for about two hours and subsequently placed in a neutral medium (pH=6.8) for the remainder of the time.

Figure 2:
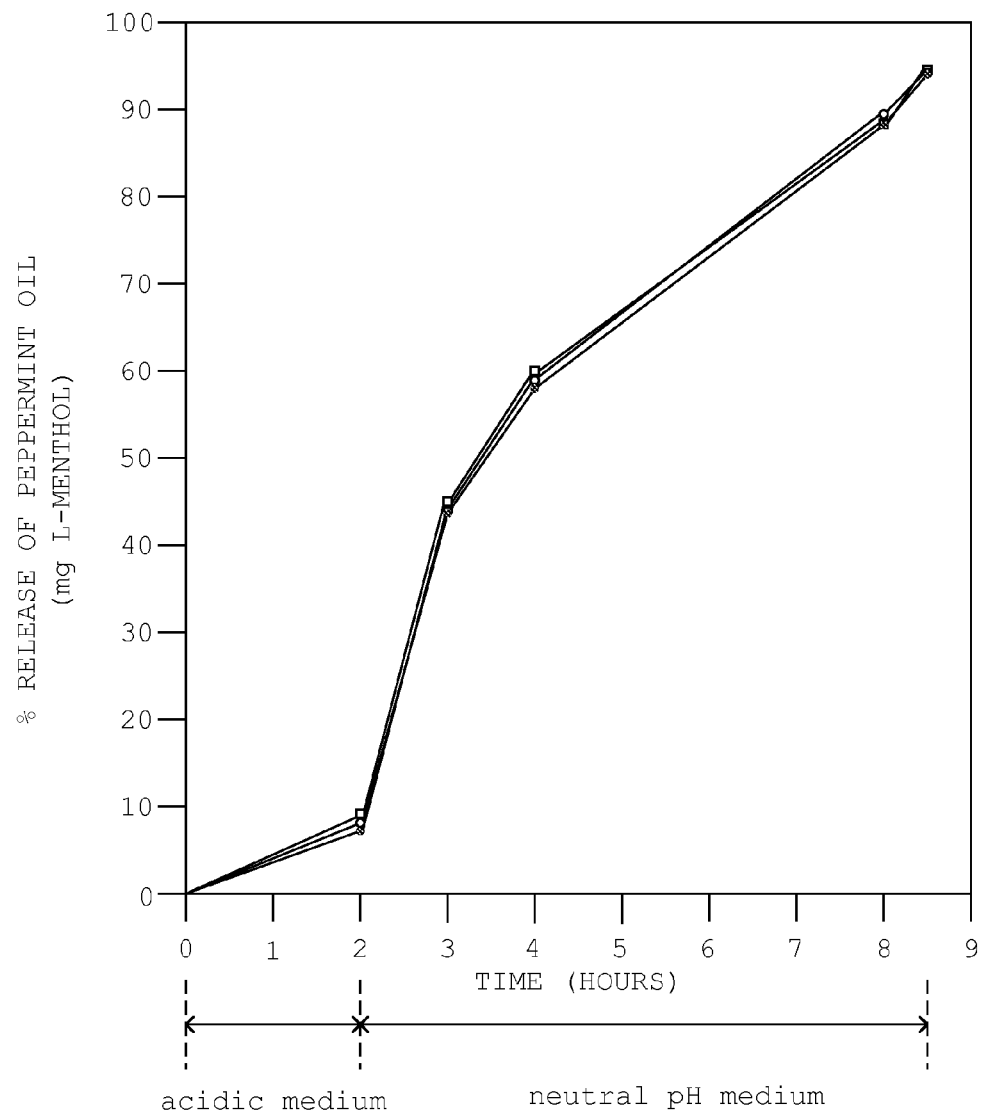
FIG. 2 is a graph showing the results of a two-stage dissolution test for a multiparticulate composition according to an embodiment after the composition was stored at 40 degrees C. and 75% relative humidity.

The results of this experiment are shown in FIG. 2 as the % release of peppermint oil, reported as the number of mgs of L-menthol over time. After two hours in the acidic medium, each of the samples tested had only released about 10% or less of the peppermint oil, indicating that the enteric coating was intact and worked normally. Over the following 6.5 hours in the neutral medium, the peppermint oil was gradually released from the core.

Unless otherwise defined, all technical and scientific terms used herein are intended to have the same meaning as commonly understood in the art to which this pertains and at the time of its filing. Although various methods and materials similar or equivalent to those described herein can be used in the practice or testing of the embodiments, suitable methods and materials are described. The skilled should understand that the methods and materials used and described are examples and may not be the only ones suitable for use.

The specification discloses typical example embodiments, and although specific terms are employed, the terms are used in a descriptive sense only and not for purposes of limitation. Example embodiments have been described in some detail, but it will be apparent that various modifications and changes can be made within the spirit and scope as described in the foregoing specification and in the claims.

That which is claimed is:

1. A storage stable L-menthol composition comprising a multiparticulate dosage form having:
    a plurality of individual cores containing crystalline L-menthol and at least one pharmaceutical excipient; and
    a proteinaceous coating of a continuous film of proteinaceous material over the cores forming a plurality of proteinaceous coated individual cores, the film being effective to substantially prevent the crystalline L-menthol from volatilizing and leaving the proteinaceous coated individual cores when stored at a temperature of 40 degrees C. and 75% relative humidity from between 1 day to 30 days;
    wherein the dosage form contains an effective amount of the crystalline L-menthol for treating a gastrointestinal disorder;
    wherein an enteric coating over the proteinaceous coated individual cores prevents the L-menthol from releasing into the stomach and allows the L-menthol to release into the intestines; and
    wherein the proteinaceous coating is 3.5% to 35% w/w of the individual enteric coated cores.

2. The storage stable L-menthol composition of claim 1, wherein the crystalline L-menthol is in the form of a polycrystalline powder.

3. The storage stable L-menthol composition of claim 1, wherein the proteinaceous material includes gelatin.

4. The storage stable L-menthol composition of claim 1, wherein the proteinaceous material includes acid bone gelatin.

5. The storage stable L-menthol composition of claim 1, wherein the enteric coating comprises a methacrylic acid based material.

6. The storage stable L-menthol composition of claim 1, wherein the at least one pharmaceutical excipient includes each of methylcellulose and microcrystalline cellulose.

7. The storage stable L-menthol composition of claim 1, wherein:
    the crystalline L-menthol is in the form of a polycrystalline powder;
    the at least one pharmaceutical excipient includes each of methylcellulose and microcrystalline cellulose; and
    the proteinaceous material includes acid bone gelatin.

8. The storage stable L-menthol composition of claim 1, wherein:
    the crystalline L-menthol is in the form of a polycrystalline powder;
    the at least one pharmaceutical excipient includes each of methylcellulose and microcrystalline cellulose;
    the proteinaceous material includes acid bone gelatin; and
    the enteric coating is methacrylic acid based.

9. The storage stable L-menthol composition of claim 1, wherein the enteric coated cores are spheroidal and have a diameter of 0.1 mm to 3 mm.

10. The storage stable L-menthol composition of claim 1, wherein the effective amount is 80 to 100 mg of crystalline L-menthol per dosage form.

11. A method of making a storage stable L-menthol composition, the method comprising preparing the composition of claim 1 by:
    forming the plurality of individual cores by combining the crystalline L-menthol and at the least one pharmaceutical excipient;
    applying the continuous film of the liquid proteinaceous material over the individual cores;
    drying the liquid proteinaceous material over the individual cores to form the proteinaceous coated individual cores; and applying the enteric coating over the proteinaceous coated individual cores.

12. The method of claim 11, further comprising preparing a tablet, caplet, capsule, or sachet dosage form having the individual enteric coated cores therein.

13. The method of claim 12, wherein the individual enteric coated cores are spheroidal and have a diameter of 0.1 mm to 3 mm.

14. The method of claim 11, further comprising, prior to forming the individual cores, micronizing L-menthol crystals by jet milling.

15. The method of claim 11, wherein the crystalline L-menthol is in the form of a polycrystalline powder.

16. The method of claim 11, wherein the liquid proteinaceous material includes gelatin and water.

17. The method of claim 11, wherein the liquid proteinaceous material is a solution containing at least about 35% gelatin.

18. The method of claim 11, wherein the liquid proteinaceous material is a solution containing at least about 50% gelatin.

19. The method of claim 11, wherein the liquid proteinaceous material includes acid bone gelatin.

20. The method of claim 11, wherein the enteric coating includes a methacrylic acid based material.

21. The method of claim 11, wherein the at least one pharmaceutical excipient includes each of methylcellulose and microcrystalline cellulose.

22. The method of claim 11, wherein the liquid proteinaceous material is applied by spraying it over the core.

23. The method of claim 11, wherein:
the crystalline L-menthol is in the form of a polycrystalline powder;
the at least one pharmaceutical excipient includes each of methylcellulose and microcrystalline cellulose; and
the liquid proteinaceous material is a solution containing at least about 35% acid bone gelatin.

24. A method of treating a gastrointestinal disorder, the method comprising:
administering to a patient in need thereof an effective amount of the composition of claim 1.

25. The method of claim 24, wherein the crystalline L-menthol is in the form of a polycrystalline powder.

26. The method of claim 24, wherein the proteinaceous material includes gelatin.

27. The method of claim 26, wherein the proteinaceous material includes acid bone gelatin.

28. The method of claim 24, wherein the enteric coating includes a methacrylic acid based material.

29. The method of claim 24, wherein the at least one pharmaceutical excipient includes each of methylcellulose and microcrystalline cellulose.

30. The method of claim 24, wherein:
the crystalline L-menthol is in the form of a polycrystalline powder;
the at least one pharmaceutical excipient includes each of methylcellulose and microcrystalline cellulose; and
the proteinaceous material includes acid bone gelatin.

31. The method of claim 24, wherein:
the crystalline L-menthol is in the form of a polycrystalline powder;
the at least one pharmaceutical excipient includes each of methylcellulose and microcrystalline cellulose;
the proteinaceous material includes acid bone gelatin; and
the enteric coating is methacrylic acid based.

32. The method of claim 24, wherein the enteric coated cores are spheroidal and have a diameter of 0.1 mm to 3 mm.

33. The method of claim 24, wherein the effective amount is 80 to 100 mg of L-menthol per tablet, caplet, capsule, or sachet dosage form.

* * * * *